(12) United States Patent
Gellman et al.

(10) Patent No.: US 7,416,533 B2
(45) Date of Patent: Aug. 26, 2008

(54) MARKING BIOPSY SITES

(75) Inventors: Barry N. Gellman, N. Easton, MA (US); Richard Tah, Framingham, MA (US); Jozeph Slanda, Milford, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 352 days.

(21) Appl. No.: 11/325,844

(22) Filed: Jan. 4, 2006

(65) Prior Publication Data

US 2006/0111646 A1 May 25, 2006

Related U.S. Application Data

(63) Continuation of application No. 10/639,945, filed on Aug. 13, 2003, now Pat. No. 7,001,341.

(51) Int. Cl.
| | |
|---|---|
| *A61B 10/00* | (2006.01) |
| *A61B 5/05* | (2006.01) |
| *A61B 6/00* | (2006.01) |
| *A61B 17/00* | (2006.01) |
| *A61B 17/08* | (2006.01) |
| *A61B 17/32* | (2006.01) |
| *A61D 1/04* | (2006.01) |
| *A61D 1/00* | (2006.01) |

(52) U.S. Cl. .............. 600/562; 600/564; 600/566; 600/567; 600/407; 600/420; 600/431; 606/116; 606/117; 606/151; 606/219; 606/167; 606/170

(58) Field of Classification Search .............. 600/562, 600/564, 566, 567, 407, 420, 431; 606/116, 606/117, 151, 219, 167, 170
See application file for complete search history.

(56) References Cited

U.S. PATENT DOCUMENTS

| | | | |
|---|---|---|---|
| 3,477,423 | A | 11/1969 | Griffith |
| 4,699,154 | A | 10/1987 | Lindgren |
| 4,832,686 | A | 5/1989 | Anderson |
| 4,958,625 | A | 9/1990 | Bates et al. |
| 5,102,391 | A | 4/1992 | Palestrant |
| RE34,056 | E | 9/1992 | Lindgren et al. |
| 5,195,533 | A | 3/1993 | Chin et al. |
| 5,853,366 | A | 12/1998 | Dowlatshahi |
| 5,868,673 | A | 2/1999 | Vesely |
| 5,967,982 | A | 10/1999 | Barnett |
| 6,056,700 | A | 5/2000 | Burney et al. |
| 6,173,715 | B1 | 1/2001 | Sinanan et al. |
| 6,220,248 | B1 | 4/2001 | Voegele et al. |
| 6,228,055 | B1 | 5/2001 | Foerster et al. |
| 6,234,177 | B1 | 5/2001 | Barsch |

(Continued)

FOREIGN PATENT DOCUMENTS

EP   1 304 085   4/2003

(Continued)

OTHER PUBLICATIONS

PCT Search Report dated Dec. 23, 2004.

*Primary Examiner*—Jeffrey G. Hoekstra
(74) *Attorney, Agent, or Firm*—Fish & Richardson P.C.

(57) ABSTRACT

A needle biopsy system for marking a sampling site is described.

13 Claims, 11 Drawing Sheets

U.S. PATENT DOCUMENTS

| | | |
|---|---|---|
| 6,261,243 B1 | 7/2001 | Mark et al. |
| 6,270,464 B1 | 8/2001 | Fulton et al. |
| 2002/0107437 A1 | 8/2002 | Sirimanne et al. |
| 2004/0236212 A1 | 11/2004 | Jones et al. |

FOREIGN PATENT DOCUMENTS

| | | |
|---|---|---|
| WO | WO 98/30166 | 7/1998 |
| WO | WO 99/58065 | 11/1999 |
| WO | WO 01/08578 | 2/2001 |
| WO | WO 01/13800 | 3/2001 |

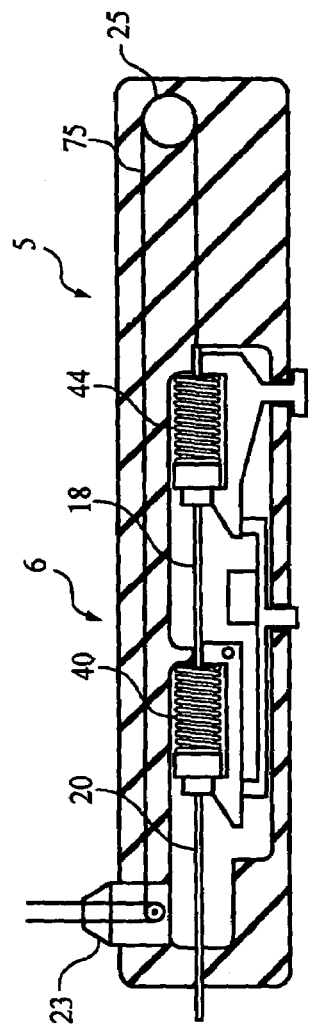
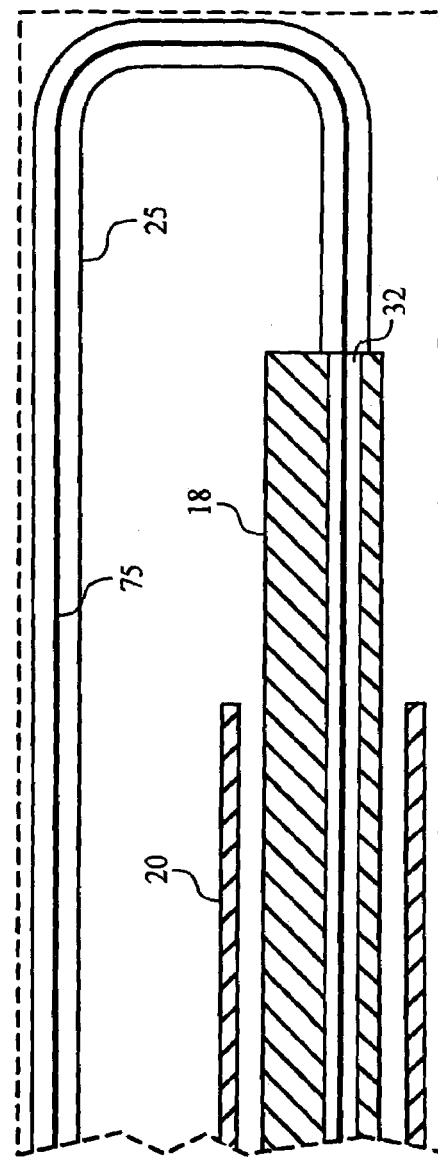

MARKING BIOPSY SITES

CROSS-REFERENCE TO RELATED APPLICATIONS

This application is a continuation of and claims priority under 35 U.S.C. §120 to U.S. application Ser. No. 10/639,945, filed Aug. 13, 2003 now U.S. Pat. No. 7,001,341, the entire contents of which being hereby fully incorporated by reference.

TECHNICAL FIELD

This invention relates to marking biopsy sites.

BACKGROUND

The invention relates to the field of biopsy devices.

A needle biopsy device is frequently used to obtain a piece of tissue for microscopic examination to determine malignancy, while subjecting the patient to the least trauma. Typically, the instrument consists of a long, thin, probe, termed a stylet, within a close-fitting hollow needle, termed a cannula. The stylet and cannula are controlled manually or by a firing mechanism that first projects the stylet into a tissue mass, followed by the cannula. The stylet has a notch into which tissue will prolapse when the stylet penetrates the tissue mass. As the cannula slides over the stylet, a small piece of tissue is severed from the tissue mass and captured within the notch of the stylet. The device is then withdrawn and the piece of tissue removed from the stylet notch. An example of a device including a two-stage actuation mechanism in which the cutting needle and cannula are advanced in timed sequence under spring actuation is described in Bates, U.S. Pat. No. 4,958,625, the entire contents of which is incorporated herein by reference.

SUMMARY

In an aspect, the invention features a needle biopsy system that includes a sampling portion locatable inside the body. The sampling portion includes a stylet having a sampling region and a cannula. The stylet and cannula are relatively moveable along the stylet axis to position the cannula over the sampling region. A sample marker is locatable in and releasable from the sampling portion.

In another aspect, the invention features a method of biopsy treatment by providing a needle biopsy device. The biopsy device includes a sampling portion with a stylet having a sampling region, and a cannula. The stylet and cannula are relatively moveable to position the stylet over the sampling region. The stylet is inserted into a tissue mass. The cannula is located over the sampling region by relative motion between the stylet and the cannula. A marker is delivered from the sampling portion into the tissue while removing the stylet from the tissue.

In another aspect, the invention features a method of biopsy treatment. The treatment includes taking multiple biopsy samples from a tissue. The location of each of the multiple samples is marked contemporaneously with the taking of each sample. A marker is released into the tissue mass. The marker is detectable by ultrasound, x-ray analysis, or magnetic resonance imaging. The tissue samples are analyzed. Tissue, corresponding to the location of at least one of the samples, is treated.

In other aspects, the invention features biopsy markers and their use as described below.

Embodiments can include one or more of the following. The sample marker is locatable between the stylet and the cannula. The biopsy system can include a marker lumen between the stylet and cannula. The marker lumen can include a supply of multiple markers in the lumen. The markers in the supply can be arranged sequentially and generally parallel to the stylet. The supply of markers can be provided radially around the stylet. The supply of markers can be rotatable relative to the stylet axis.

The marker lumen can include a marker exit opening adjacent the distal end of the stylet. The stylet can include a side notch and the exit opening can be distal of the side notch. The opening can be oriented to eject a marker substantially parallel to the stylet. The stylet can include a side notch and a marker exit opening proximal of the side notch. The stylet can include a side notch and at least one marker exit opening aligned with an end of the side notch. A first exit opening can be located adjacent a first axial periphery of the sampling region and a second exit opening can be located adjacent a second axial periphery of the sampling region. The exit opening can be in the cannula.

The biopsy system can include a control handle portion. The controller can include a supply of markers. The system can include a marker pusher to selectively locate markers in the sampling portion. The pusher can be actuated from the handle portion. The marker can be indicative of the axial length of a tissue region from which a sample is taken. The marker can include an elongated element. The elongated element can include regions along its length distinguishable by MRI, ultrasound or fluoroscopy. The distinguishable regions can be spaced to indicate the length of a tissue region from which a sample is taken. At least a portion of the marker can be bio degradable.

The biopsy system can include a supply of markers. A given marker can be distinguished by MRI, ultrasound or fluoroscopy from another marker in the supply. The marker can include a tissue engaging edge that resists proximal motion of the marker when the marker is in contact with the tissue.

A marker can be magnetically fixed to the exterior of the stylet. The marker can be axially translatable by motion of the cannula to release the marker. The marker can be translated to a location where it is magnetically repulsed from the cannula.

The method can include inserting the stylet into the tissue mass a second time and delivering a second marker into the tissue mass. The markers can be distinguished by ultrasound, fluoroscopy or magnetic resonance.

The method can include correlating the markers with the location of the multiple tissue samples. The method can include analyzing the samples for abnormal indication, and treating a portion of the tissue mass. The method can include analyzing the tissue samples for cancerous indication.

Embodiments may include one or more of the following advantages. The biopsy device can take biopsy samples at various sites in the body, for example, in the prostate, and concurrently deliver a marker, such as a radiopaque marker, to the site. The marker can be delivered to the site through the sampling portion of the biopsy device so that the device does not have to be removed before marker placement. The marker can be deployed to indicate the ends of the site. The marker can be at least partially biodegradable. When several samples (e.g., 3-12) are taken, the device can deliver markers that can be distinguished from one another by e.g. ultrasound, fluoroscopy, MRI or a combination of techniques. For example, the markers can be differently shaped and/or sized radiopaque markers. Marking the biopsy site facilitates non-invasive and continued monitoring of the biopsy site, which enables effective treatment strategies to be devised. For example, a therapeutic device or agent can be guided by and located between the markers to tract a site.

The details of one or more embodiments of the invention are set forth in the accompanying drawings and the description below. Other features, aspects, and advantages of the invention will be apparent from the description and drawings, and from the claims.

Like reference symbols in the various drawings indicate like elements.

BRIEF DESCRIPTION OF DRAWINGS

FIG. 2A is a cross-sectional view of the control handle of the device of FIG. 1.

FIG. 2B is a cross-sectional side view illustrating the path of a pusher through a guide tube, stylet and cannula within the control handle in FIG. 1.

FIG. 3E illustrating the device after initiation of marker deployment; and FIG. 3F illustrating the device being withdrawn from the body and the marker being placed in the biopsy site.

DETAILED DESCRIPTION

Structure

Figure 1:
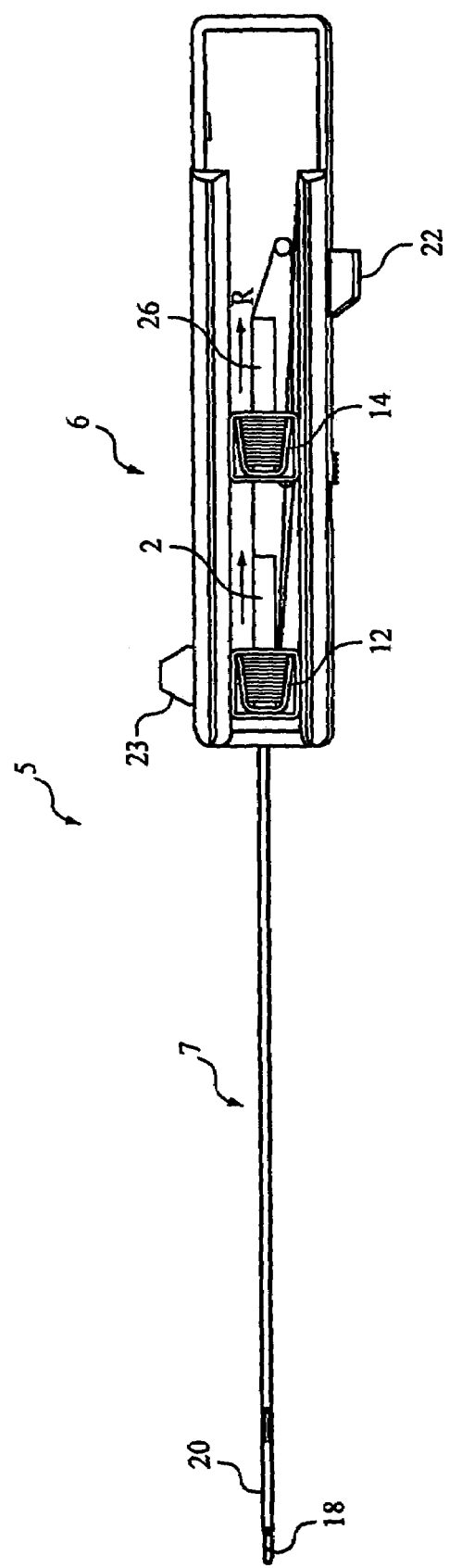
FIG. 1 is a side view of an embodiment of a needle biopsy device.

Referring to FIGS. 1-2B, a biopsy device 5 includes a control handle 6 and a sampling portion 7. The sampling portion 7 includes a stylet 18 with a sample notch 30 and a concentrically arranged cannula 20. The stylet 18 and cannula 20 project from the control handle 6. To take a sample, the stylet 18 and the cannula 20 are retracted to an armed condition using control buttons 12, 14 on the control handle 6. The retracted stylet and cannula compress respective springs 44 and 40 in the control handle 6. The sampling portion 7 is located adjacent the tissue from which a sample is to be taken. The device is fired by actuating a firing button 22 which releases the stylet spring 44, causing the stylet 18 to be extended such that it pierces a tissue mass. The cannula spring 40 is subsequently released to extend the cannula 20 which severs a sample from the tissue mass. The sample is captured in the sample notch 30 on the stylet 18.

During the sampling procedure, the device can be monitored inside the body or tissue mass by, e.g., ultrasound, fluoroscopy or MRI. After a sample is taken, the device is removed from the body and the sample retrieved from the notch for analysis. Organs in which this procedure can be carried out include the prostate, kidney, uterus, breast, or other suspected tumor sites. The sampled area can be treated as needed, e.g., by tissue ablation therapy using RF ablation, induction heating, interstitial laser ablation, hypothermia therapy, cryotherapy, alcohol injection, and administration of a sclerosing agent. Typically these techniques include delivering a catheter or other instrument to locally treat the area around the biopsy site and avoid damaging adjacent healthy tissue. The treatment can also be monitored by ultrasound, fluoroscopy or MRI. A suitable firing arrangement is described in Bates '675, incorporated supra.

Figure 2C:
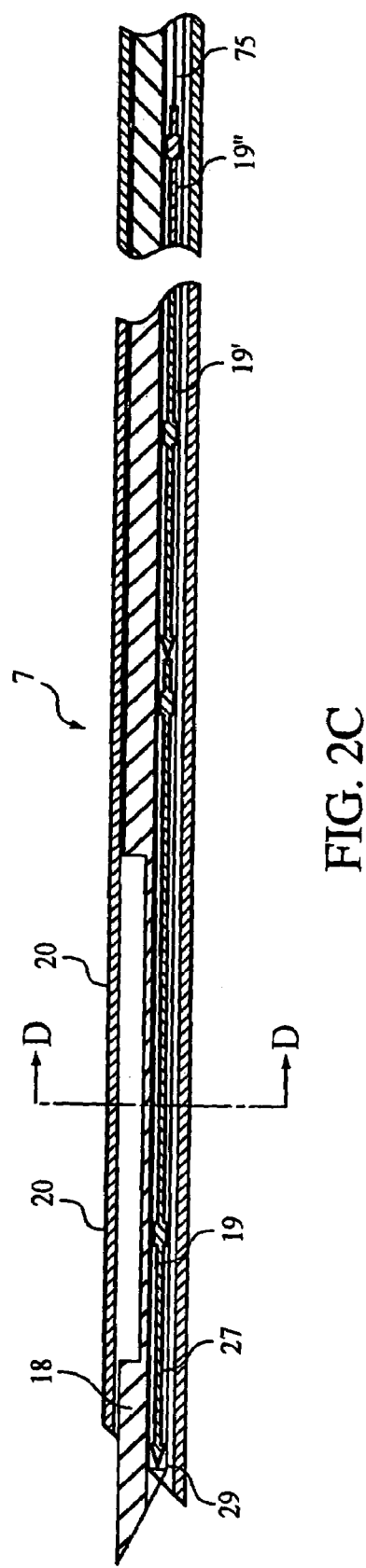
FIG. 2C is a cross-sectional view of the sampling region of the device of FIG. 1.
Figure 2D:
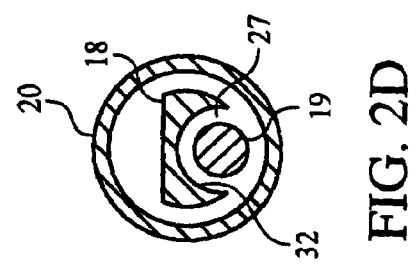
FIG. 2D is a cross-sectional view taken along D-D of FIG. 2C.

Referring particularly to FIGS. 2C and 2D, the sampling portion 7 carries multiple elongated markers 19, 19', 19" etc. The markers 19, 19', 19" are located end to end in a lumen 27 that is substantially parallel to the axis of the stylet 18. The lumen 27 terminates at its distal end in an opening 29 through which the markers can be ejected, as will be described below. The lumen 27 is defined by a slot 32 on the outer surface of the stylet 18 and the inner surface of the cannula 20 (FIG. 2D).

Referring as well to FIG. 2A, a pusher 75 is controlled by a slide 23 on the control handle. Referring particularly to FIG. 2B, an enlarged view which illustrates the path of the pusher into the lumen 27 in the control handle with other components removed, the pusher 75 is directed by a guide tube 25 to the groove 32 at the proximal end of the stylet. Referring particularly to FIG. 2C, the distal end of the pusher 75 engages the proximal end of the most proximal marker 19". By actuating the slide 23 proximally the pusher 75 moves distally so that the markers 19, 19', 19" are pushed distally, and the most distal marker 19 is ejected through opening 29.

Figure 2E:
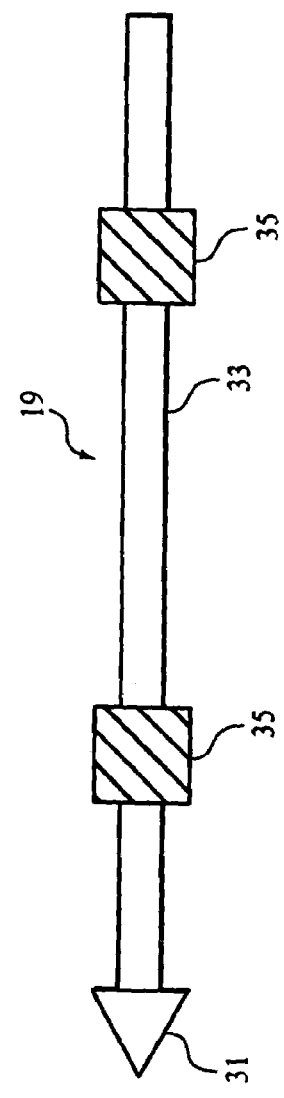
FIG. 2E is side view of a marker.

Referring particularly to FIG. 2E, each marker 19, 19', 19" includes a rod portion 33, a tip portion 31, and two bands 35, 35'. The bands 35, 35' can be distinguished from the rod portion 33 by ultrasound, fluoroscopy, and MRI. The bands 35, 35' are fixed to and spaced along the rod portion 33 at a distance that approximately equals the length of the stylet notch 30 and can thus indicate the extension of a sampling site. In addition, the rod portion 33 maintains the bands 35, 35' in a defined orientation relative to one another so that the relative plane or perspective of the bands 35, 35' as viewed by ultrasound, etc., is detectable. In addition, the marker bands 35, 35' and the tip portion 31 have a larger cross-section than the rod portion 33, which facilitates a friction fit of the markers in the lumen 27 so that they are not prematurely ejected. The larger profile also inhibits motion of the markers after deployment in the body.

The bands 35, 35' can be made of a material that is detectable by diagnostic technique(s) such as ultrasound, MRI, and x-ray fluoroscopy. For radiopaque marker bands, a high density metal such as tantalum, platinum, gold, or stainless steel can be used. In embodiments, materials with a density of 10 g/cc or more can be used. The bands can be solid metal or a metal combined in polymer matrix. For ultrasound visibility, metal bands can be used and/or coatings of materials, e.g., polymers, differentiatable based on acoustic impedance can be used. For MRI detection, materials having different resonant signatures, e.g., different magnetic susceptibility can be used. Examples include materials that produce a magnetic field that disrupts T1 or T2 of surrounding protons. Suitable materials include paramagnetic and ferromagnetic materials, such as gadulinium-based materials and iron-based materials. A supply of markers can be provided such that each marker has a band or bands or associated shapes, which can be differentiated from the bands on other markers so that multiple biopsy sites can be readily distinguished. For example, for radiopaque bands, the paired bands on different markers may have different identifying configurations (circular, lines or rings, such as one line/ring at either end of the bands or two lines/rings at either end, triangular, square, donut, hex, etc.) or sizes. In embodiments, the bands on each marker can also be distinguishable from one another by shape, size or material. Bands on different markers or the bands on a given marker may be constructed to enhance visibility by different diagnostic techniques. For example, one band may include a high density metal to enhance radiopacity for fluoroscopic visibility, while another band includes a ferromagnetic material for enhanced MRI visibility.

In embodiments, the tip 31 and rod 33 portions can be made of a polymer, such as a bioabsorbable or biodegradable polymer, e.g., polylactic acid and polyglycolic acid. In embodiments, the biodegradable polymer dissolves rapidly leaving the less or generally non-degradable marker bands in the body for viewing over a longer period of time. In the embodiment illustrated, the tip portion 31 has a triangular cross-sectional shape which has a gradual taper that facilitates distal motion into tissue but resists proximal motion. Other tip portion shapes include hook-shapes and barbs. The tip portion can be a continuous extension of the rod portion. The tip and rod portions can be formed, e.g., by molding. The bands can be attached, e.g., by an adhesive. In embodiments, the bands can be integral with the rod, e.g. molded of the same polymer. In embodiments, the tip and/or rod portions can be made to enhance visibility by diagnostic techniques as discussed above. For example, the tip and/or rod can be metal or include a metal.

In an embodiment the overall length of the marker is about 0.75 inches. The diameter of the rod portion is about 0.005-0.006 inches. The marker bands have an axial width of about 0.03 inches and a spacing (inner edge to inner edge) of about 0.6 inches. The markers and the tip portion have a maximum diameter of about twice the rod diameter. A suitable cannula and stylet have a length of about 10 inches, and can accommodate, e.g., 4-6 markers.

The pusher 75 can be made of a material with sufficient column strength to transmit the force needed to eject the markers. The pusher 75 also has sufficient flexibility to follow a circuitous path in the handle. Suitable materials include metal wire made, for example, of a highly flexible metal such as nitinol, or polymer filament. The pusher 75 can be directed along a path in the handle defined, e.g., by a guide tube 25. The guide tube guides the pusher around a clockwise path and directs the pusher into the stylet slot at the proximal end of the stylet. The amount of slide motion for marker ejection can be indicated by visual marks or detents on the control handle. Slide 23 can include a lock, e.g., an element moveable in the slide path, to prevent motion of slide 23. The lock can be engaged, e.g., after one marker has been ejected, to prevent more than one marker from being placed at one biopsy site. In other embodiments, rather than following a path entirely in the control handle, the pusher may extend from the proximal end of the control handle and be urged distally by linearly pushing it into the control handle and the lumen 27.

Use

Figure 3A:
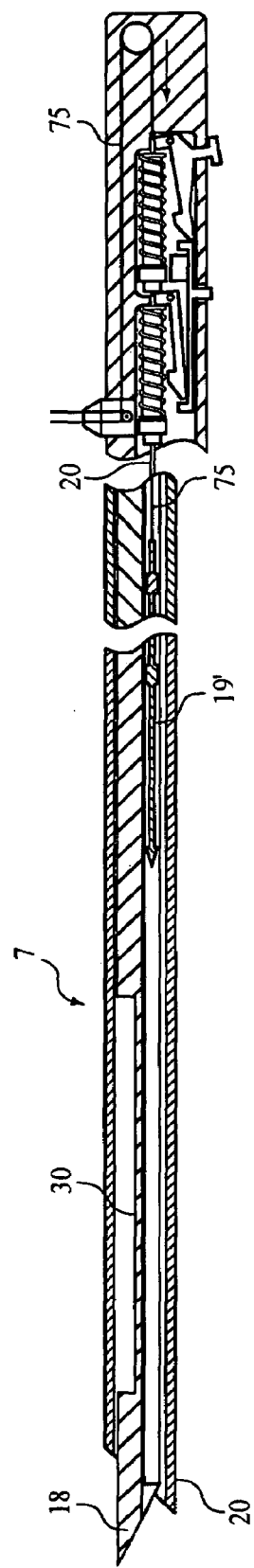
FIGS. 3A-3F are expanded cross-sectional views of the control handle and the sampling region of the device of FIG. 1, with FIG. 3A illustrating the device in neutral condition before sampling, FIG. 3B illustrating the device with the stylet and cannula both armed, FIG. 3C illustrating the device after the stylet has been fired and the cannula armed, FIG. 3D illustrating the device after the cannula has been fired.

Referring now to FIG. 3A et seq., a biopsy procedure including placement of a marker at the site of tissue removal is illustrated. Each figure illustrates expanded cross-sectional views of the control handle 6 and the sampling region 7.

Referring to FIG. 3A, the device is in the neutral position, e.g., prior to use. The stylet 18 and cannula 20 are both extended with the cannula 20 covering the sample notch 30 of stylet 18. The sampling portion includes a supply of markers 19, 19', 19" etc., in the lumen 27. The markers 19, 19', 19" can be loaded into the lumen 27 through the opening 29. The markers are pushed into the lumen 27, e.g. using a wire so that the end of pusher 75 is adjacent the proximal end of the most proximal marker 19".

Figure 3B:
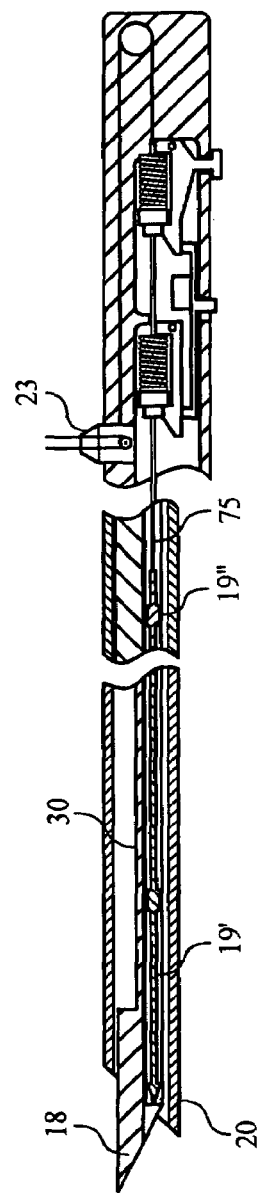

Referring to FIG. 3B the cannula 20 and stylet 18 are armed for firing. In this condition, the stylet 18 and cannula 20 have been retracted toward the control handle 6.

Figure 3C:
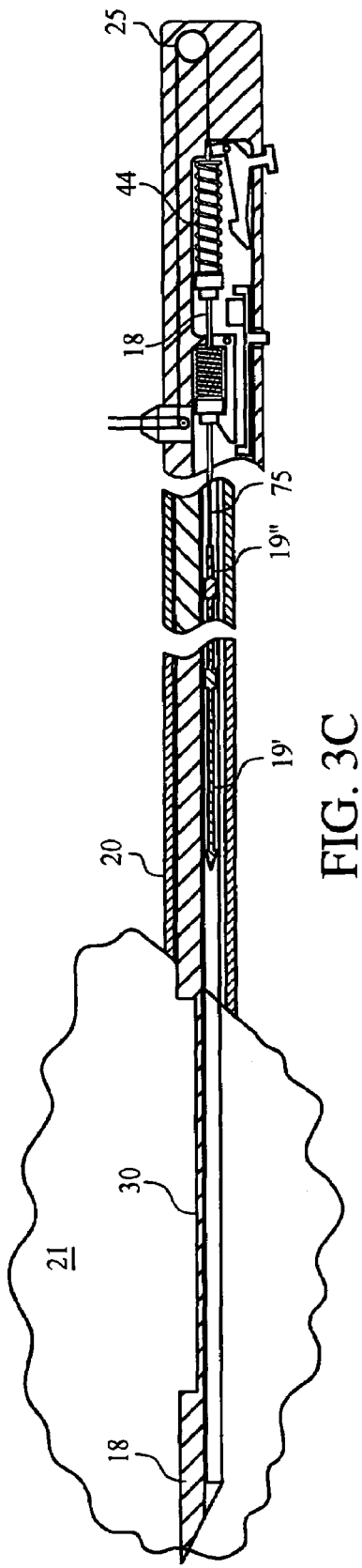

Referring to FIG. 3C, to take a sample, the stylet 18 is fired, causing the stylet 18 to project into a tissue mass 21.

Figure 3D:
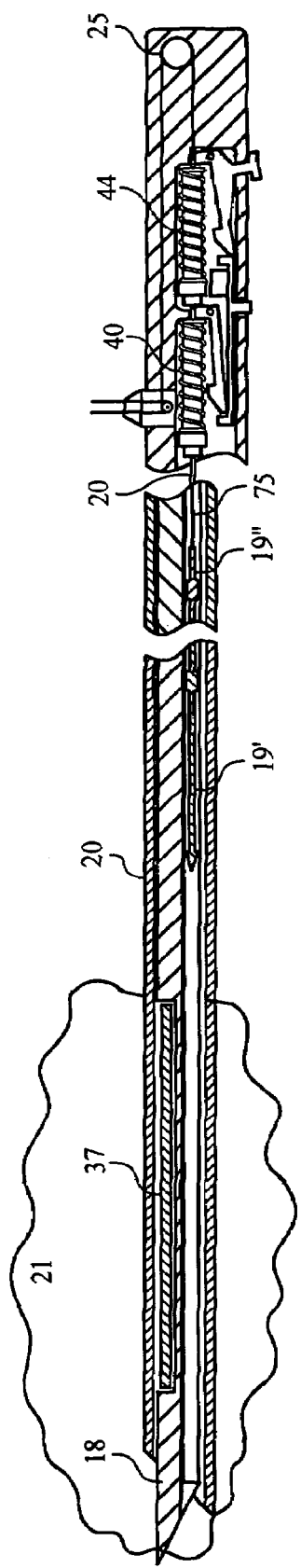

Referring to FIG. 3D, the cannula 20 is fired. The cannula 20 severs a sample 37 from the tissue, which prolapses into the notch 30 of stylet 18. (Because of the rapid motion of the cannula, the markers in the lumen 27 remain substantially in the same location as the stylet 18 and cannula 20 are fired).

Figure 3E:
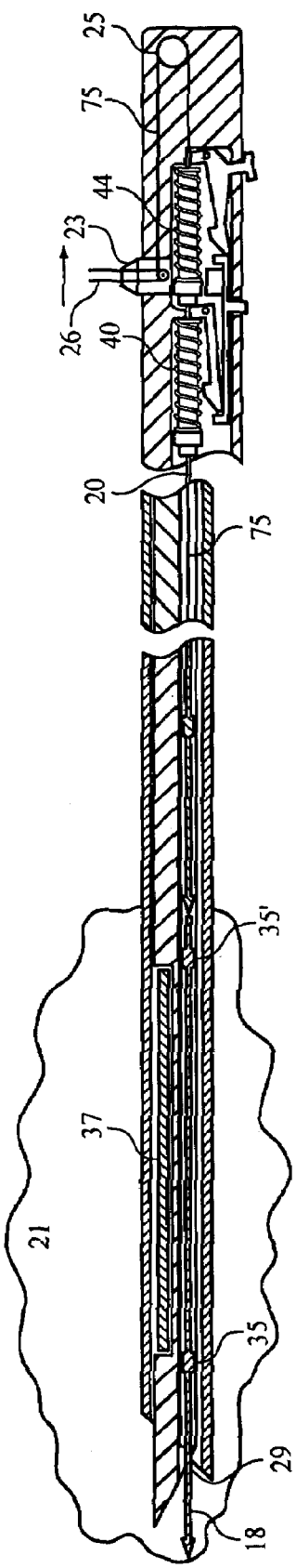

Referring to FIG. 3E, without removing the device from the body, a marker is placed at the biopsy site by moving slide 23 toward the proximal end of control handle 6 (arrow). This motion of slide 23 moves pusher 75 through guide 25 around a clockwise path, and then distally in the lumen 27, pushing the markers 19, 19', 19" distally. Slide 23 is moved a distance such that the bands 35, 35' on marker 19 are approximately at the proximal and distal ends of the notch 30 and the marker tip 31 is exposed from the opening 29. The marker tip 31 engages the tissue adjacent the distal end of the sampling site and lodges the marker at the site.

Figure 3F:
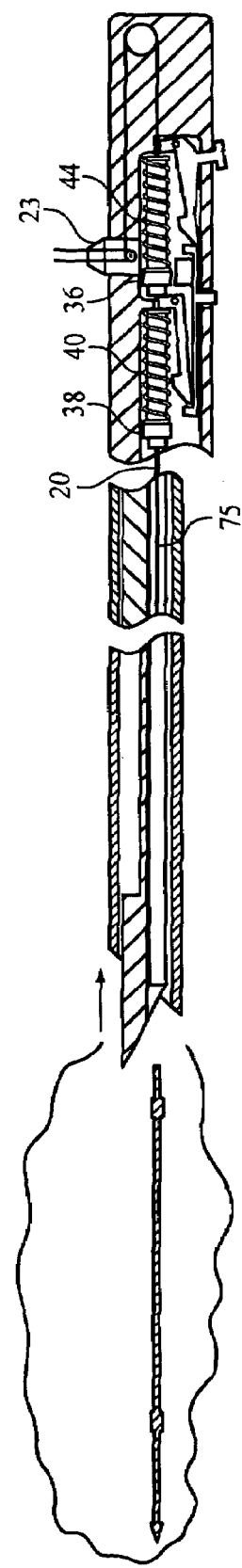

Referring to FIG. 3F, the sampling portion 7 is withdrawn. As the sampling portion 7 of device 5 is withdrawn from the site (arrow), the marker position is maintained by the tip 31. The bands 35, 35' remain positioned at the two ends of the biopsy site. Alternatively, the pusher 75 may be activated to completely eject a marker at or near the site, e.g. as the device is being removed.

OTHER EMBODIMENTS

Figure 4A:
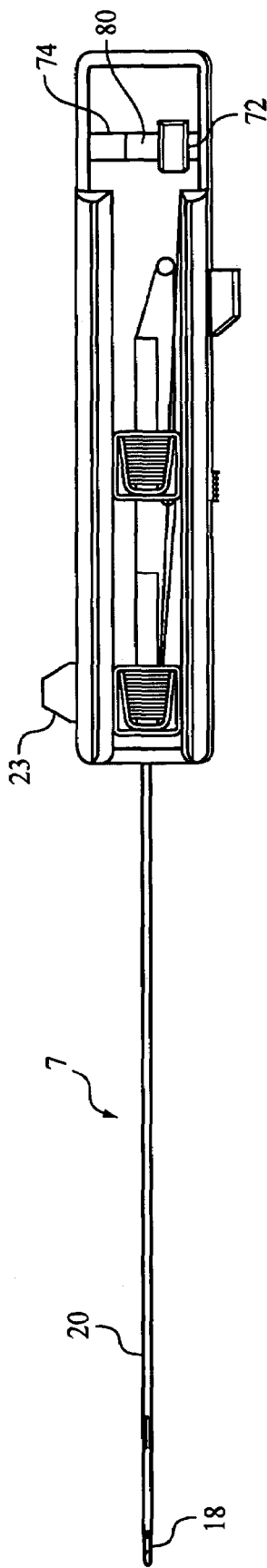
FIG. 4A is a side view of another embodiment of a needle biopsy device.
Figure 4B:
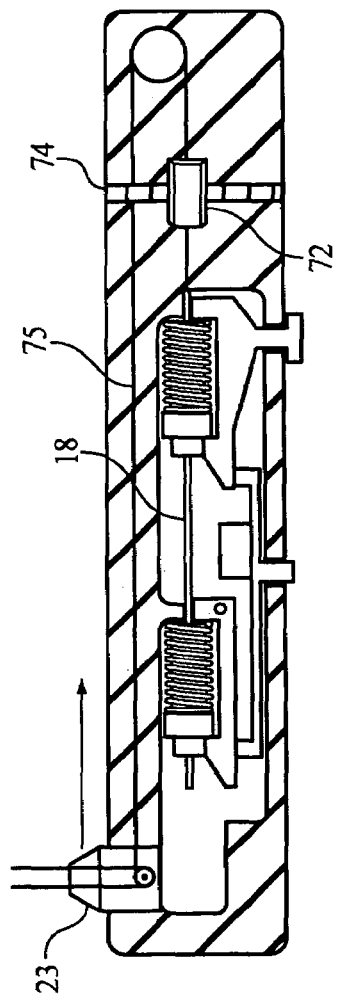
FIG. 4B is a cross-sectional side view of the control handle of the device of FIG. 4A.
Figure 4C:
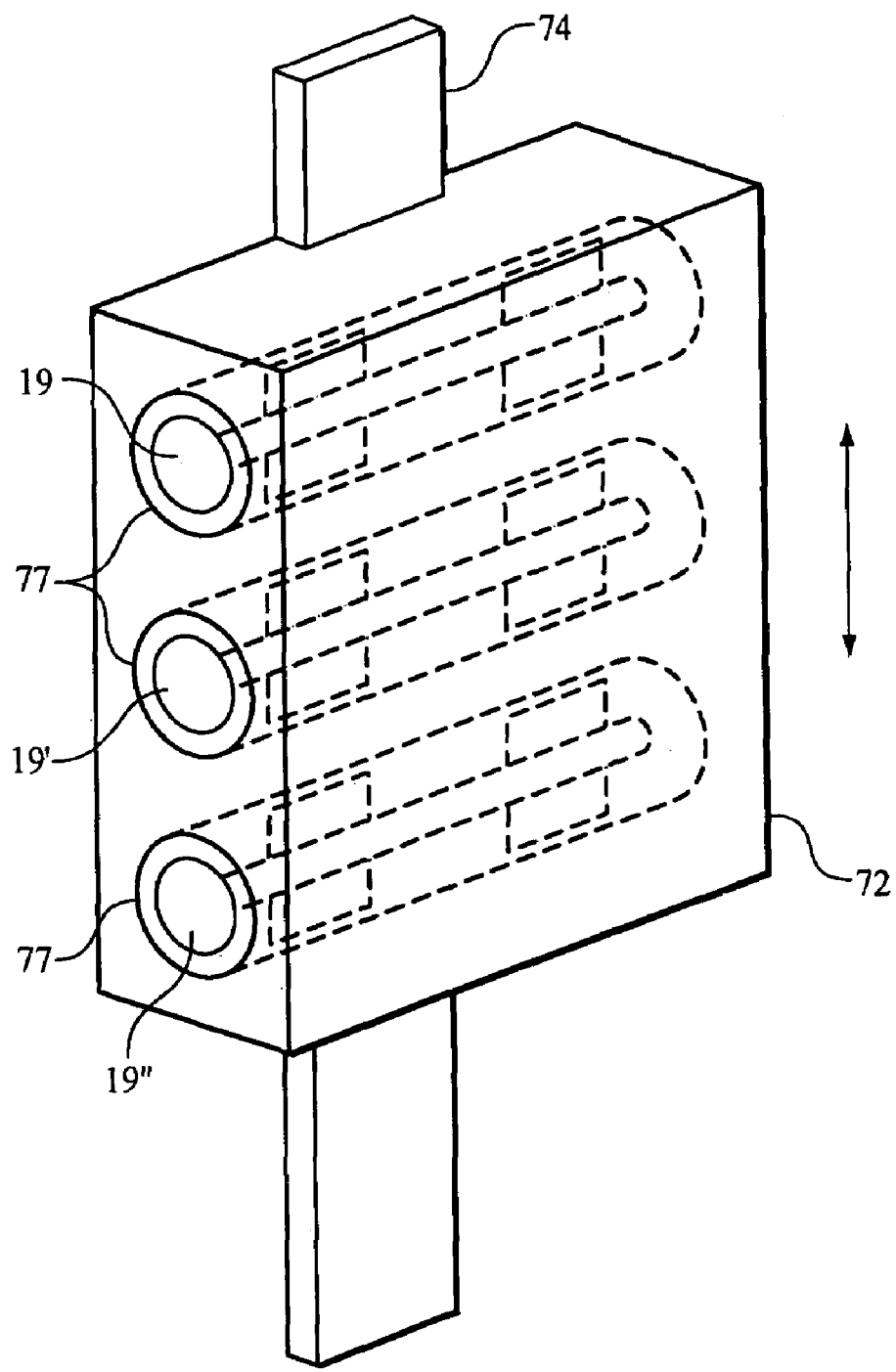
FIG. 4C is a perspective expanded view of a marker cartridge.

Referring to FIGS. 4A-C, in another embodiment, a supply of markers is carried in a control handle. The control handle includes a marker cartridge 72, which includes lumens 77 that hold markers 19, 19', 19". The marker cartridge 72 can be moved along a railing 74 using a slide button 80 so that a slot containing a marker is axially aligned with the lumen 27 of stylet 18. Pusher 75 is actuated so that the distal end of the pusher enters a slot in the cartridge to push the marker from the cartridge into the lumen 27, and to eject marker through opening 29 into the site. After a marker placement, the pusher is retracted so its distal end is proximal of the cartridge, and the marker cartridge is slid along the railing 74 placing another slot containing a marker in alignment with lumen 27. A subsequent sample can then be taken and the site marked.

Figure 5A:
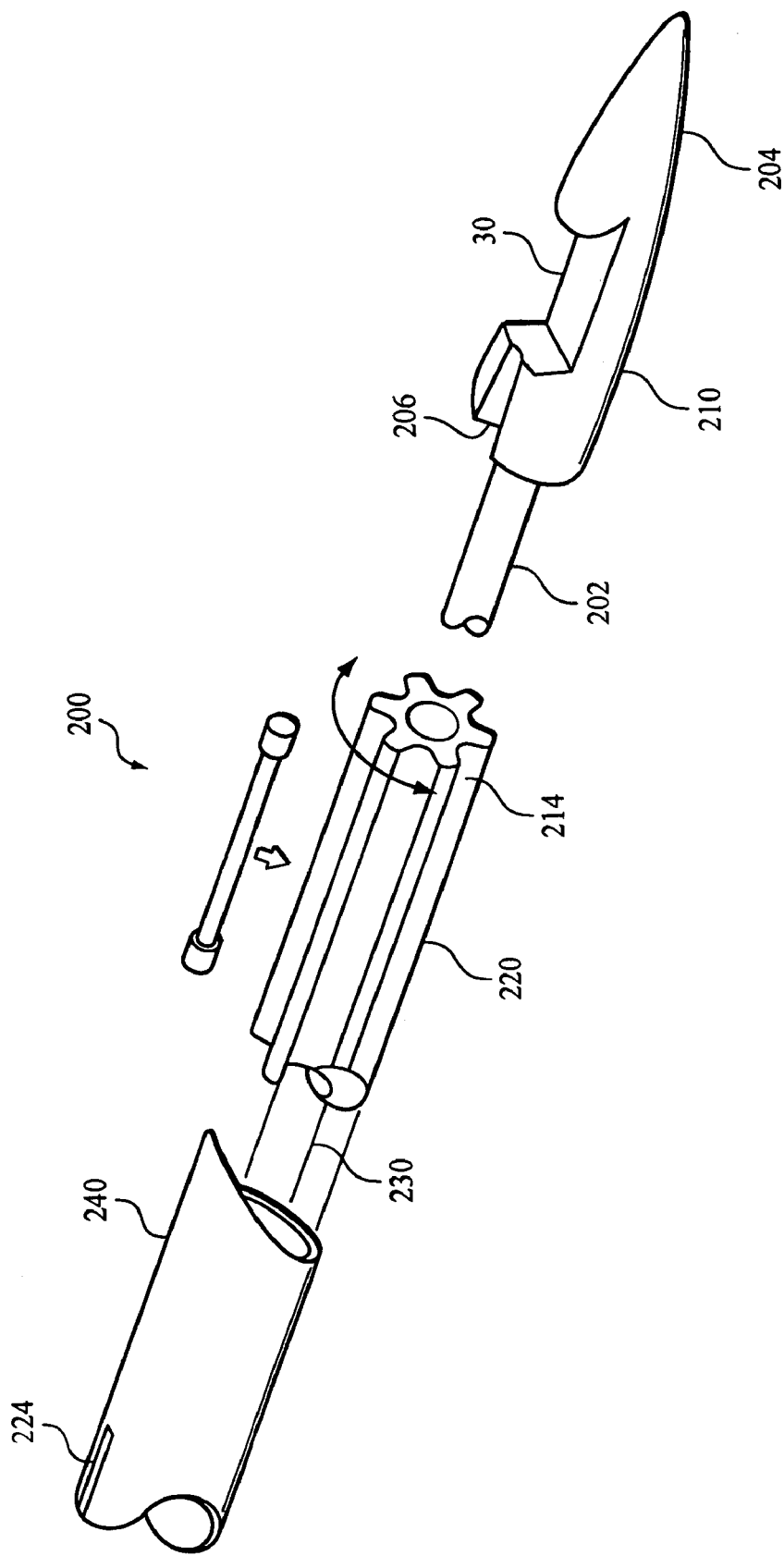
FIG. 5A is an expanded perspective view of the sampling region in another embodiment of the needle biopsy device.
Figure 5B:
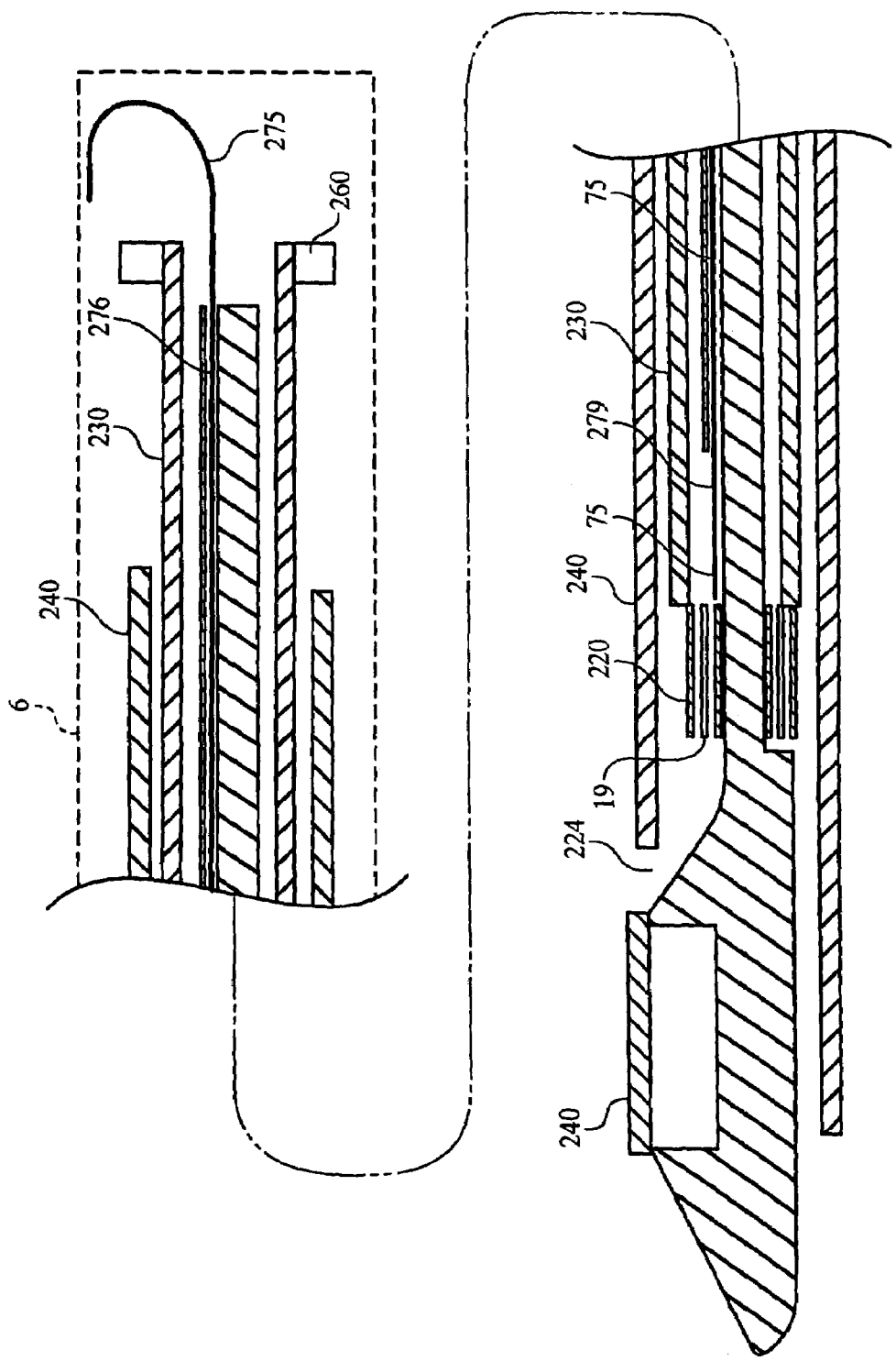
FIG. 5B is a cross-sectional view of components in a control handle and a sampling region in the embodiment of FIG. 5A.
Figure 5C:
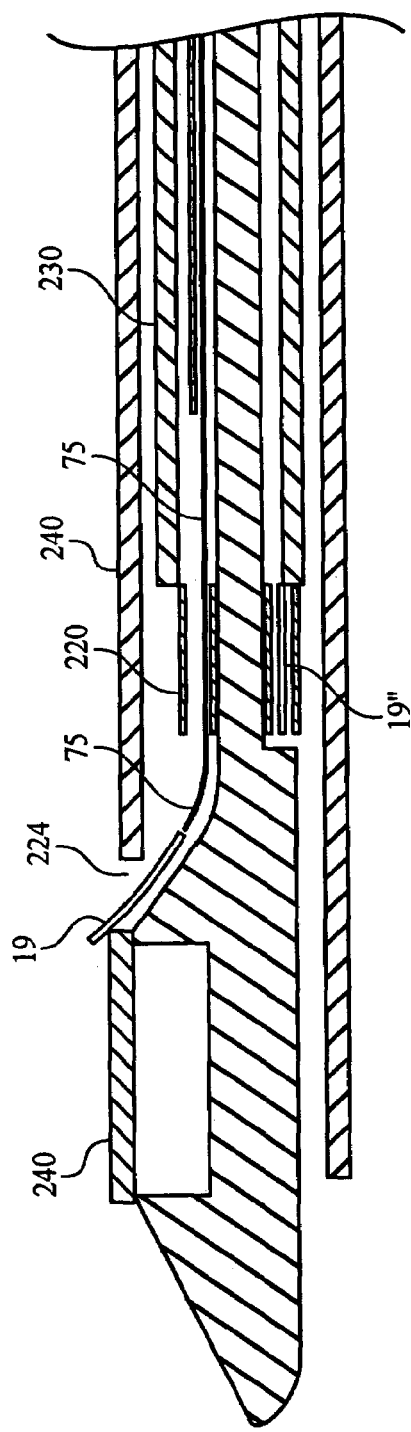
FIG. 5C is a cross-sectional view of components in the sampling region in the embodiment of FIG. 5A.

Referring to FIGS. 5A-5C, in another embodiment, a sampling region 200 includes a stylet 210, a rotary cartridge 220, a rotary control tube 230 and a cannula 240. The stylet 210 includes a body 202 that extends to a tip 204. The tip 204 has a sample notch 30 and a marker guide 206. The cartridge 220 is rotatably positioned over the stylet body 202. The rotation control tube 230 extends from the proximal end of cartridge 220. The cartridge 220 has a plurality of slots 214, to accommodate markers 19. The slots 214, and the markers 19 contained within the slots, can be sequentially brought into axial alignment with the marker guide 206 on the stylet tip 204 by rotating cartridge (arrow) relative to the stylet. The cannula 240 has a marker opening 224 through which markers can be ejected.

Referring to FIG. 5B, when the cannula 240 is extended distally to cover the notch in the stylet tip 204, the marker opening 224 of cannula 240 is vertically aligned with the marker guide 206 of stylet tip 204. The guide 206 is angled, (e.g. 25-50°) to guide a marker through the opening 224. A pusher 275 enters a slot 276 in the proximal end of the stylet body. The pusher 275 extends through the stylet body to an opening 279 proximally adjacent the cartridge 220. Referring to FIG. 5C, after a sample is taken, the pusher 275 can be actuated distally to slide a marker from the cartridge slot 214 to the marker guide 206 of stylet tip 204. The marker is ejected through the marker opening 224 and placed at the sampling site.

To mark another sample site, the pusher is retracted from the cartridge, and the rotation control tube 230 is actuated. The rotation control 230 includes at its distal end the cartridge 220. The tube 230 is arranged concentrically over the stylet body and extends proximally to the control handle and terminates in a control knob 260. The control knob 260 can protrude through the control handle body where it can be accessed by the user. By rotating the control knob 260, the user can rotate the cartridge 220 to bring marker grooves 214 sequentially into alignment with the marker guide 206. In addition, the control knob 260 can be retracted proximally to retract marker cartridge 220 proximally when the stylet is armed. The control knob 260 can be extended distally after the device has been fired to position the cartridge 220 adjacent the marker guide 206. Alternatively, the control tube and cartridge can be retracted with the stylet. In the embodiment described above, the marker is ejected at a radial location corresponding to the location of the stylet notch. In embodiments, the pusher and guide can be arranged to eject the marker at other radial locations, e.g. 180° opposite the notch.

Figure 6:
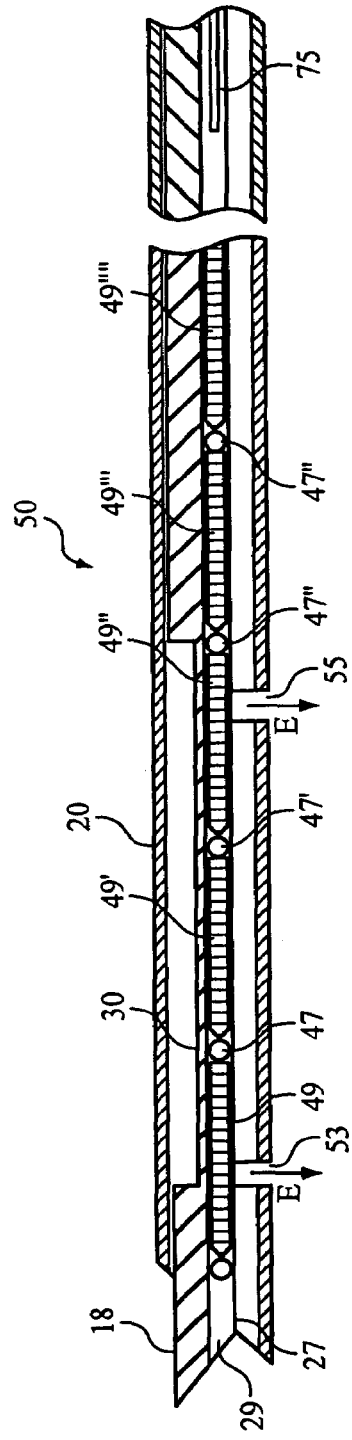
FIG. 6 is a cross-sectional side view of the sampling region in another embodiment of a needle biopsy device.

Referring to FIG. 6, in another embodiment, a sampling region 50 includes discrete bands 47, 47', 47" etc., which are spaced by separate rods 49, 49', 49" etc., within lumen 27. In this embodiment, the bands are not fixed to rods. Cannula 20 has two apertures 53 and 55 positioned adjacent the ends of the stylet notch 30 when the cannula is over the notch 30.

Marking a biopsy site is accomplished as follows. After severing a sample and without removing the device from the body, bands 47, 47', 47", and rods 49, 49', 49", are moved distally (e.g., using a pusher 75) such that the bands are brought into alignment with and fall through aperture 53 and aperture 55 (by gravity), marking the ends of a biopsy site. Sets of bands may be shaped or otherwise modified to differentiate multiple sites. The rods are ejected from the opening 29 of the lumen 27.

Figure 7A:
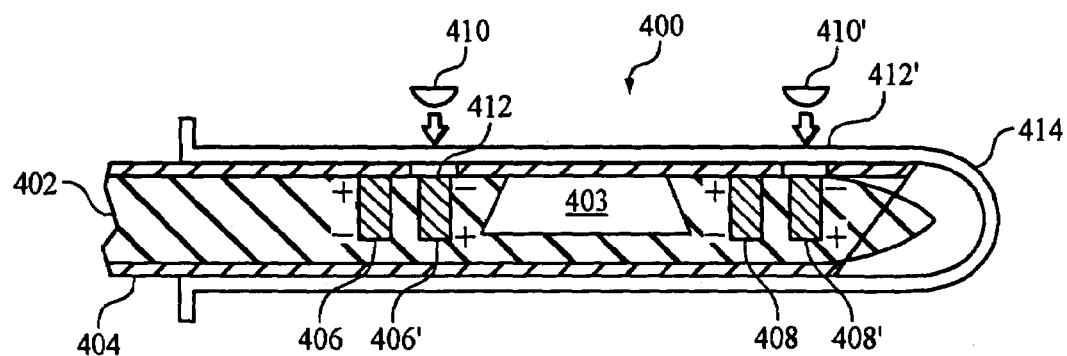
FIGS. 7A and 7B are cross-sectional side views of the sampling region in another embodiment of a needle biopsy device.
Figure 7B:
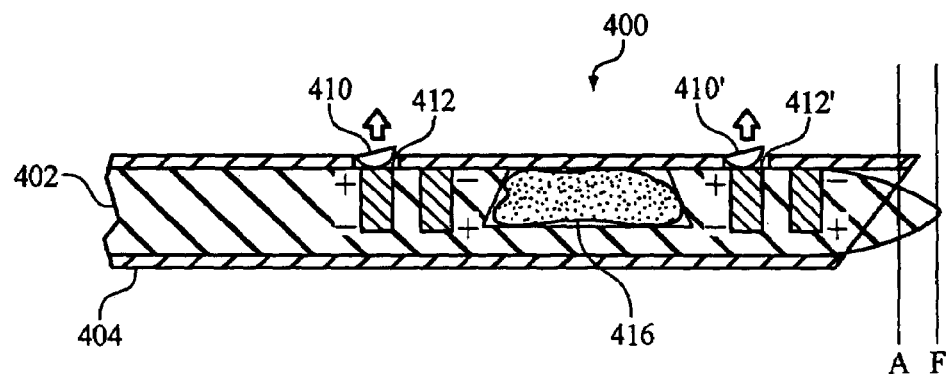

Referring to FIGS. 7A and 7B, in another embodiment, a sampling portion 400 includes a stylet 402 and a cannula 404. The stylet 402 includes a sample notch 403. The stylet includes two pairs of magnets 406, 406', and 408, 408' on either side of the notch 403. Magnets 406, 408, are oriented to have their positive poles outwardly directed and magnets 406', 408', have their negative poles outwardly directed. The device also includes magnetic marker bands 410, 410' (exploded in FIG. 7A). The cannula includes openings 412, 412' from which the bands 410, 410' can be released when the bands are aligned with repellant magnetic poles.

Referring particularly to FIG. 7A, the device is illustrated in an armed condition. An optional protective sheath 414 can be provided. The bands 410, 410' are positioned in the cannula openings 412,412' and aligned with magnet poles to which they are attracted. In this example, bands are attracted to the negative poles on magnets 406', 408'.

Referring particularly to FIG. 7B, the sampling portion is illustrated after the device has been fired and a tissue sample 416 has been captured in the notch 403. In the post-fired condition, the cannula openings 412, 412' and the bands 410, 410' are aligned with the positive poles of magnets 406, 408, which repel the bands. The bands are thus repelled by the magnets and exit the cannula opening to mark the sampling site. The relative position of the stopped cannula between FIGS. 7A and 7B is controlled by, e.g., a stop in the control handle that limits the extension of the cannula or stylet in the fired condition. In the example illustrated, in the armed condition, the stylet and cannula are in alignment at point A. In the fired condition, the stylet extends relative to the cannula to point F.

In embodiments, the shape of the band is dish-shaped (concave) with the rim being at a higher elevation than the center and located with the rim edge closest to the outside diameter of the cutting cannula outside diameter. The device actuation advances the biopsy needle into the tissue, followed in a timed sequence by the cutting cannula. The repelling force need be only strong enough to cause the dish radiopaque marker to cock slightly, raising the leading edge above the cutting cannula surface. This provides a cam surface to help strip the band from the device and maintain a marker on both ends of the tissue sample.

Figure 8:
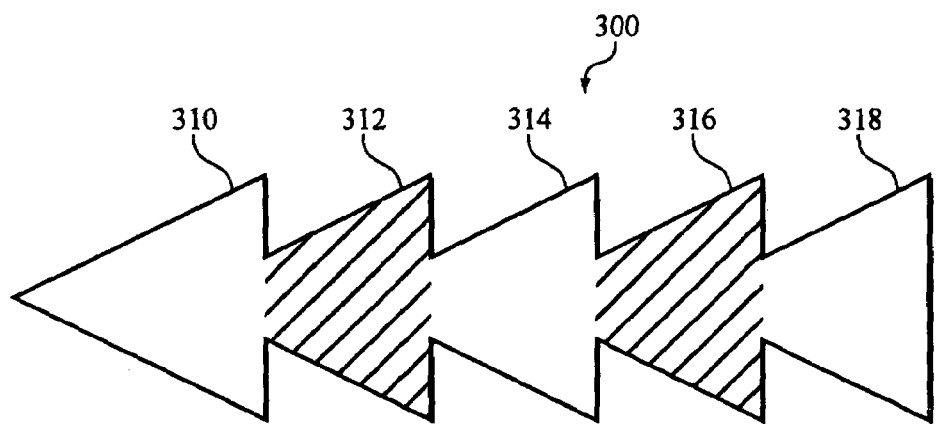
FIG. 8 is a schematic of a marker.

Referring to FIG. 8, a marker 300 is illustrated. The marker 300 includes a series of adjacent barbs 310, 312, 314, 316, 318 along its body. Barbs 312, 316 are constructed for enhanced diagnostic visibility compared to barbs 310, 314, 318, as discussed above with respect to marker bands. The spacing between the barbs 312, 316 may be selected, e.g. to indicate the length of a sampling site.

Still other embodiments are within the claims. For example, a rotary cartridge holding multiple markers can be used in the embodiment of FIG. 4 et seq.

What is claimed is:

1. A needle biopsy system, comprising:
    a sampling portion locatable inside a body and including a stylet having a sampling region and a cannula, the stylet and the cannula being relatively moveable along a stylet axis to position the cannula over the sampling region, and
    a first marker locatable in and releasable from the sampling portion;
    wherein the stylet is magnetically attractive to the first marker at a first location along the stylet and is magnetically repulsive to the first marker at a second location along the stylet; and
    the first marker is axially translatable by motion of the cannula from the first location to the second location.

2. The system of claim 1 wherein the cannula includes an aperture sized to receive the first marker.

3. The system of claim 2 wherein the first marker has a concave surface.

4. The system of claim 1 further comprising:
    a first magnet at the first location; and
    a second magnet at the second location;
    wherein the first and second magnets are arranged in the stylet with a first specified magnetic pole of the first magnet and a second opposing magnetic pole of the second magnet being proximate a surface of the stylet.

5. The system of claim 1 wherein the stylet includes a side notch.

6. The system of claim 5 wherein the second location is located adjacent a first axial periphery of the sampling region.

7. The system of claim 5 further comprising a second marker;
wherein the stylet is magnetically attractive to the second marker at a third location and is magnetically repulsive to the second marker at a fourth location; and the second marker is axially translatable by motion of the cannula from the third location to the fourth location.

8. The system of claim 7 wherein the fourth location is located adjacent a second axial periphery of the sampling region.

9. The system of claim 7 wherein the first marker is distinguishable from the second marker by ultrasound, fluoroscopy or magnetic resonance.

10. A needle biopsy system, comprising:
a sampling portion locatable inside a body and including a stylet having a sampling region and a cannula, the stylet and cannula being relatively moveable along a stylet axis to position the cannula over the sampling region, and
a first marker and a second marker, the markers locatable in and releasable from the sampling portion;
wherein the stylet is magnetically attractive to the first marker at a first location along the stylet and to the second marker at a third location along the stylet, and the stylet is magnetically repulsive to the second marker at a second location along the stylet and to the second marker at a fourth location along the stylet; and
the first marker is axially translatable by motion of the cannula from the first location to the second location and the second marker is axially translatable by motion of the cannula from the third location to the fourth location.

11. The system of claim 10 wherein the cannula includes apertures sized to receive the markers.

12. The system of claim 11 wherein the stylet includes a side notch.

13. The system of claim 12 wherein the second location is located adjacent a first axial periphery of the sampling region and the fourth location is located adjacent a second axial periphery of the sampling region.

* * * * *